United States Patent [19]
Lee et al.

[11] Patent Number: 5,542,281
[45] Date of Patent: Aug. 6, 1996

[54] METHOD FOR TESTING THE ABRASION PROPERTY AND MEASURING FRICTION COEFFICIENT OF CIRCUMFERENTIAL SURFACE OF CYLINDRICAL OBJECT AND APPARATUS FOR THE SAME

[75] Inventors: Kwang-Ryeol Lee; Kwang-Yong Eun, both of Seoul, Rep. of Korea

[73] Assignee: Korea Institute of Science and Technology, Seoul, Rep. of Korea

[21] Appl. No.: 432,067

[22] Filed: May 1, 1995

[30] Foreign Application Priority Data

May 3, 1994 [KR] Rep. of Korea ................ 94-9687

[51] Int. Cl.$^6$ .................................................. G01N 3/56
[52] U.S. Cl. .................................................................. 73/9
[58] Field of Search .................. 73/7, 9, 10, 862.55, 73/862.391

[56] References Cited

U.S. PATENT DOCUMENTS 2,910,863  11/1959  Hornbostel et al. ................ 73/7
3,324,719   6/1967  Segrave ............................. 73/9

OTHER PUBLICATIONS

Division of Ceramics, Korea Institute of Science and Technology, Kwang–Ryeol Lee, et al., "Measurement of Friction Coefficients Between Diamond–Like Carbon Coated VCR Head Drum and VCR Tapes".
Wear, vol. 93, pp. 81–99, 1984, Bharat Bhushan, "Influence of Test Parameters on the Measurement of the Coefficient of Friction of Magnetic Tapes"Testing of Metallic and Inorganic Coatings, ASTM STP 947, pp. 310–319, 1987, Bharat Bhushan, "Overview of Coating Materials, Surface Treatments, and Screening Techniques for Tribological Applications–Part2: Screening Techniques".

Primary Examiner—Robert Raevis
Attorney, Agent, or Firm—Oblon, Spivak, McClelland, Maier & Neustadt, P.C.

[57] ABSTRACT

The present invention relates to a method and an apparatus for testing the surface properties, i.e., abrasion property, friction coefficient, lubrication property, etc., of cylindrical object, e.g., VTR head drums, photocopier or laser printer drums, sewing machine spindles, fishing rod reels, etc. The apparatus of the present invention provides: a mounting means upon which a specimen of cylindrical object and a relative specimen of a flexible material is mounted and which can measure tension; a motor control unit which is connected to said mounting means so as to enable control; an amplifier electrically connected to a tension meter of said mounting means; and a computer, electrically connected to said amplifier and said motor control unit, which has been programmed to record at timed intervals the motor rotation speed and the estimated tension values, and organizes and controls all of the above said parts. Further, said mounting means including a motor where cylindrical specimen is positioned and whose revolution may be accurately controlled; a tension meter wherein each end of said relative specimen is mounted where said relative specimen is wrapped around said specimen so that at least of part of the flexible material is in contact with said specimen; and a tension meter support upon which said tension meter is mounted. According to the present invention, the abrasion and lubrication properties of cylindrical object with respect to the relative material, such as magnetic recording tape, paper, wire, etc., which could not be gauged with previous methods, may be evaluated.

8 Claims, 5 Drawing Sheets

– Before Testing –

– After Testing –

METHOD FOR TESTING THE ABRASION PROPERTY AND MEASURING FRICTION COEFFICIENT OF CIRCUMFERENTIAL SURFACE OF CYLINDRICAL OBJECT AND APPARATUS FOR THE SAME

BACKGROUND OF THE INVENTION

1. Field of the Invention

The present invention relates to a method and an apparatus for estimating properties of a cylindrical object; in particular, to a method and an apparatus for measuring the abrasion and friction coefficient between flexible materials, such as magnetic recording tape, paper, thread, etc., and said cylindrical object.

As the need for the use of materials in harsh conditions increases, improvement of the abrasion resistance and lubrication properties of the materials is required. Thus, in measuring the reliability of materials, the testing of materials' abrasion and friction coefficients is very important. Further, where a coating is applied to materials to improve abrasion resistance and lubrication, it is imperative to evaluate the properties and reliability of the coating layer. From such testing results, the development of the coating layer, improvement of the properties, and development and improvement of synthetic processes may be achieved.

2. Description of the Prior Art

To evaluate the abrasion resistance of materials, various methods exist, such as ball-on-disk testing, pin-on-disk testing, scratch testing, etc. However, the above methods can only be applied to materials with flat surfaces. Further, the materials to be used in the testing, (i.e., ball, pin, and indentor) are severely limited as to their composition and shape. One example of this is shown in FIG. 1, which is a schematic view of a testing apparatus using the pin-on-disk testing method. [Testing of Metallic and Inorganic Coatings (Ed. W. B. Harding and G. A. DiBari) pp. 310, STP 947, ASTM, Philadelphia, Pa. (1987)] In FIG. 1, reference numeral 11 denotes the pressure rod which is the relative testing material and reference numeral 12 denotes the rotational disk test specimen. As seen in FIG. 1, rotational disk testing object 12 must have a flat surface configuration. The information which may be obtained through such testing is limited to the friction coefficient and abrasion resistance between the testing object and the relative testing material in the shape of a ball or pin. Further, although abrasion property testing methods such as the pin on cylinder method, rectangular flats on rotating cylinder method, four-ball method, crossed-cylinder method, disk-on-disk method, etc., have been proposed for testing objects with cylindrical or ball shapes, the shape of the relative testing materials is still limited.

SUMMARY OF THE INVENTION

The object of this invention is to overcome the above shape-related difficulties and to provide an apparatus and a method for evaluating the abrasion properties and friction coefficient of circumferential surfaces of cylindrical object.

The above object is achieved by providing a method for testing an abrasion property and evaluating friction coefficient for a cylindrical specimen around of which circumferential surface a relative specimen of flexible material is wrapped, comprising the following steps of: (a) wrapping the relative specimen of the flexible material around the circumferential surface of the cylindrical specimen so that at least some portion of the flexible material is in contact with the circumferential surface of the cylindrical specimen; (b) applying a predetermined tension to the relative specimen; (c) rotating the cylindrical specimen while the relative specimen remains stationary; (d) measuring tension at both ends of the relative specimen; (e) evaluating the difference between the tension values at both ends of the relative specimen; and (f) evaluating the friction coefficient between the circumferential surface of the cylindrical specimen and the relative specimen using the difference of the tension value.

Additionally, the object of this invention is achieved by an apparatus for evaluating the abrasion properties and friction coefficient of a drum or a cylindrical object which has a flexible material wrapped around its body or circumferential surfaces of the object, comprising a mounting means upon which a cylindrical specimen and a relative specimen of flexible material are mounted; a motor control unit which is controllably connected to said mounting means; an amplifier electrically connected to said mounting means; and a computer, electrically connected to said amplifier and said motor control unit, which is programmed to record at timed intervals the motor rotation speed and the estimated tension values. The mounting means comprises a motor where said cylindrical specimen is positioned and whose revolution may be accurately controlled; a tension meter wherein both ends of the relative specimen, which is wrapped around said cylindrical specimen so that at least of part of the flexible material is in contact with the cylindrical specimen, are mounted; and a tension meter support, upon which said tension meter is mounted, are provided. Further, the cylindrical specimen is mounted on said motor whose revolution may be controlled; said relative specimen is wrapped around the body of said cylindrical specimen; said cylindrical specimen is rotated while said relative specimen remains stationary; and after minute electric signals from said tension meter installed at both ends of said relative specimen being transmitted through said amplifier to be read by said computer means. Simultaneously, said computer calculate the friction coefficient between the surface of the specimen and relative specimen using the differences in said read tension values.

Examples of products of cylindrical object of which abrasion resistance and lubrication properties are important factors include VTR head drums, photocopier or laser printer drums, sewing machine spindles, and fishing rod reels. When such products are used, the relative material which creates abrasion or friction are usually magnetic tape, paper, string, etc., and the abrasion or lubrication property between such relative materials and cylindrical object cannot be measured using conventional methods. Further, abrasion and lubrication properties depending on the relative material used, and it is desirable to conduct testing under conditions as similar as possible to actual conditions of use. The present invention sets forth the inventive feature of enabling an evaluation of the properties between circumferential surface of a cylindrical object and flexible relative materials such as tape, paper, wire, etc.

PREFERRED EMBODIMENTS OF THE INVENTION

The present invention is explained further in detail below by referring to the Figures.

Figure 1:
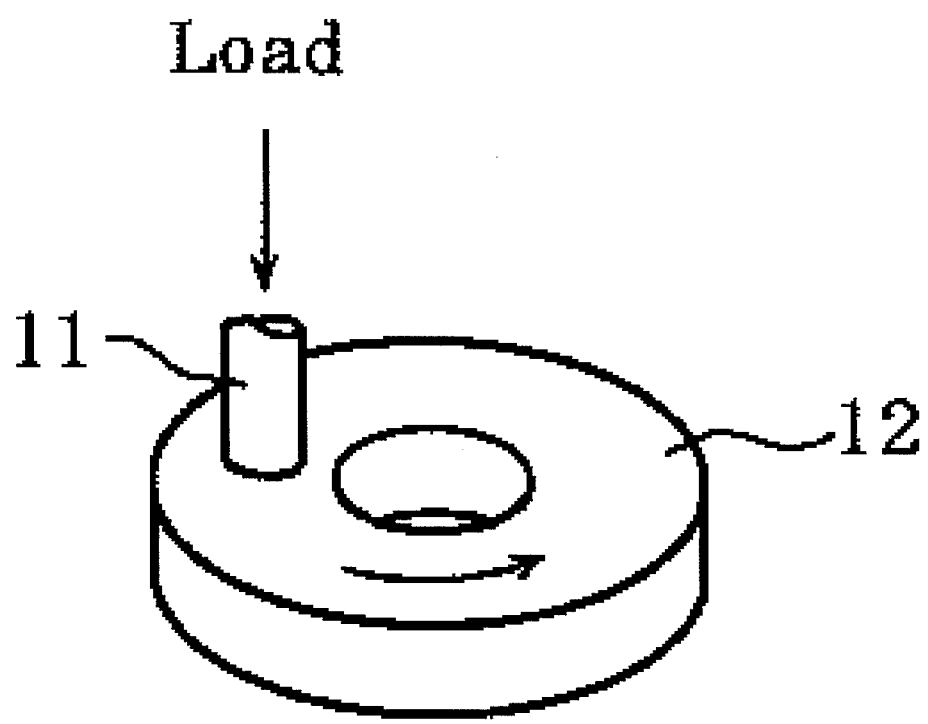
FIG. 1 is a schematic view of an apparatus for abrasion resistance and friction coefficient testing using the pin on disk method.
Figure 2:
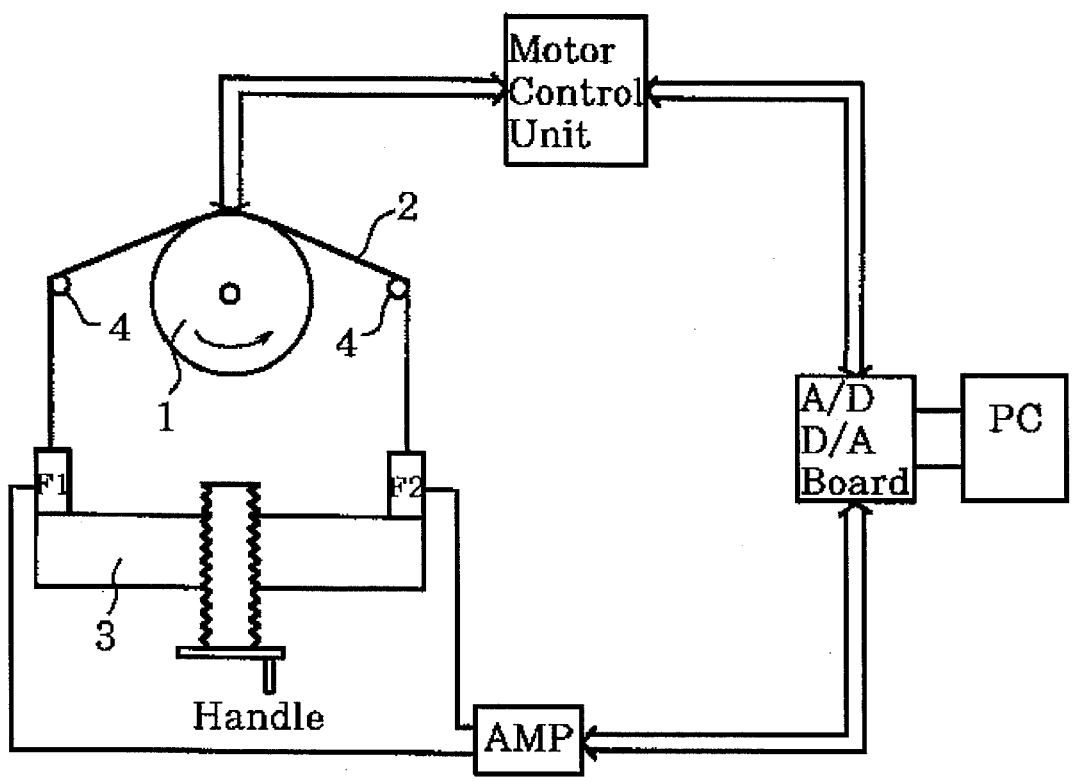
FIG. 2 is a schematic view of the apparatus for abrasion resistance and friction coefficient testing of the present invention.

FIG. 2 is a schematic structural view of the apparatus of the present invention for evaluating the abrasion resistance properties and measuring friction coefficients.

The apparatus according to the present invention is device of evaluating an abrasion property and measuring friction coefficient for a circumferential surface of cylindrical object, comprising: a mounting means which mounts a cylindrical object specimen 1 and relative specimen 2 which is a flexible material, such as tape, paper, string, etc., and measures tension; a motor control unit which is controllably connected to said mounting means; an amplifier which is electrically connected to a tension meter on said mounting means; and a computer which is electrically connected to said amplifier and said motor control unit, and which is programmed to record the motor rotation speed and estimated tension values at timed intervals, and collect and organize all of the above information. Said mounting means comprises a motor upon which said relative specimen is positioned and whose rotation speed may be accurately controlled; tension meters $F_1$ and $F_2$, upon which each end of the relative specimen, which is wrapped around the cylindrical specimen so that at least some portion is in contact with the specimen, is mounted; a tension meter support 3 upon which said tension meters $F_1$ and $F_2$ are mounted.

Cylindrical specimen 1 is mounted on a servo motor whose rotation speed may be controlled at up to several thousand revolutions per minute (rpm). Here, the center axis of cylindrical specimen 1 and the motor axis must be exactly aligned in order for the tension meter to accurately measure tension values without fluctuation. The relative specimen 2 to be used in the testing is contacted with the surface of specimen 1 with a constant tension force but the contacting area may be controlled by changing the position of tie bar 4. Each end of relative specimen 2 is mounted on a highly sensitive tension meter $F_1$ and $F_2$. Said tension meters $F_1$ and $F_2$ are mounted on tension meter support 3 which may be moved forward and backward to control the applied tension. The rotation speed of the motor is controlled in real time by a combination of the motor control unit and the computer. The minute electric signals originating from said tension meters $F_1$ and $F_2$ are amplified 1000 times by said amplifier to be read by said computer. Said computer is programmed so that rotation speed of the motor and measured tension values are recorded at timed intervals to obtain the testing results.

Where the apparatus of the present invention is operated to conduct abrasion property testing and friction coefficient measuring, the relative specimen 2 to be used for the testing is mounted on the cylindrical specimen 1 so that at least some portion of the relative specimen 2 contacts the surface of the cylindrical specimen 1. Further, each end of said relative specimen 2 is mounted on a tension meters $F_1$ and $F_2$; the tension meter support 3 supporting said tension meters $F_1$ and $F_2$ are moved to apply the desired tension on said relative specimens; the rotation speed and time period for the abrasion testing are controlled by said computer; and said cylindrical specimen 1 is rotated while the relative specimen 2 remains stationary. Here, where the cylindrical specimen 1 is rotated at high speeds, an air gap forms between the cylindrical specimen 1 and the relative specimen 2. In this regard, instantaneous stopping and instantaneous rotation may be repeated to create physically complete contact between the cylindrical specimen and relative specimen. To achieve this, the control of the motor through the use of a computer is required. After the testing is completed, the weight and the surface condition of the cylindrical specimen tested are analyzed to evaluate the degree of abrasion. Also, the friction coefficients before and after the abrasion testing are evaluated to estimate the change in lubrication property from the abrasion.

The principles behind using the apparatus of the present invention to evaluate the friction coefficient is as follows.

When the motor is not rotating, tension meters $F_1$ and $F_2$ at both sides show the same tension value. When the motor is rotating, a difference in tension values shown by the two tension meters result. This difference in tension value is correlated to the friction coefficient. In FIG. 2, if the rotational direction of the motor is counter-clockwise, the tension reading in tension meter $F_1$ decreases from when there is no rotation, and the tension reading in tension meter $F_2$, in contrast, increases. Thus, the above difference in tension readings may be used to calculate the friction coefficient.

Figure 3:
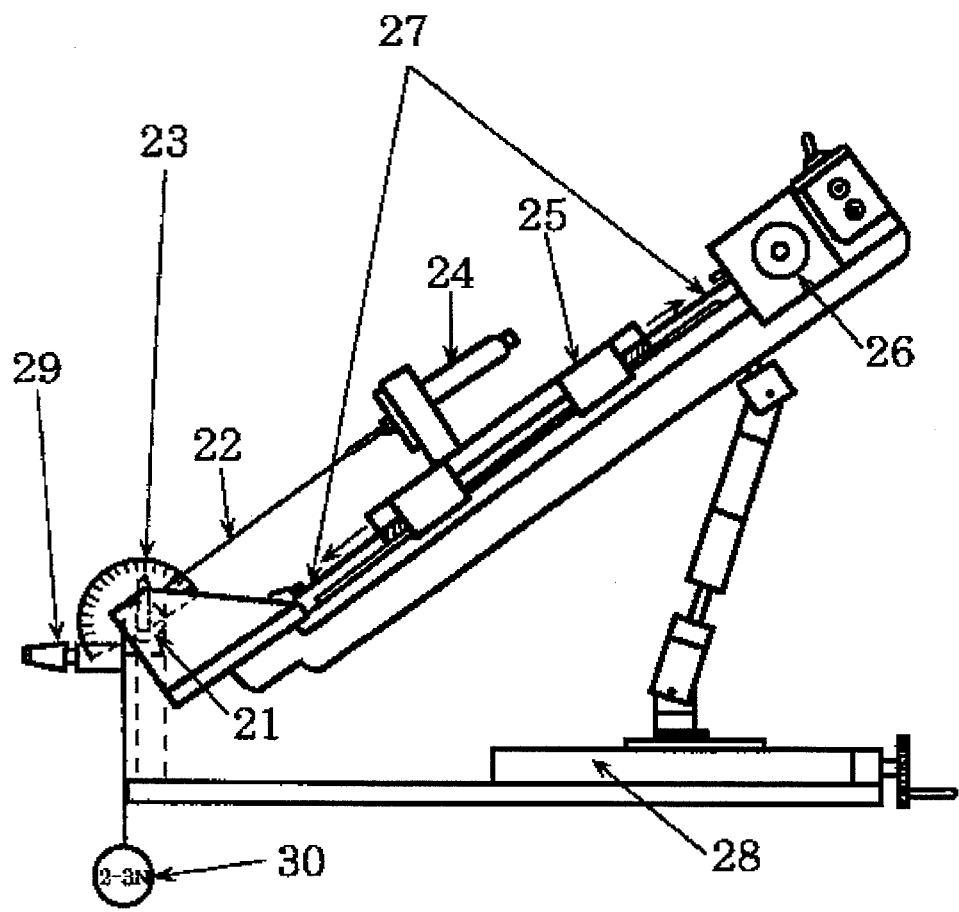
FIG. 3 is a schematic view of an apparatus for abrasion resistance testing using the prior art Bhushan method.

Bhushan proposes an apparatus, as shown in FIG. 3, to estimate the friction coefficient between the head and tape in a computer magnetic recording system. In FIG. 3, reference numeral 21 denotes the rod which is testing object made of materials of the head; reference numeral 22 denotes the tape which is the relative testing material; reference numerals 23 denotes the protractor for wrap-angle indication which indicates the wrap-angle of contact between said tape 22 and said rod 21; reference numeral 24 denotes the tension meter upon which said tape 22 is mounted; reference numeral 25 denotes a slider which can slide said tension meter 24 in a front-to-back direction; reference numeral 26 denote the motor; reference numeral 27 denotes a cable which aids the sliding motion of said slider 25, of which one end is mounted on a pulley and the other end is mounted on a movable roller of said motor 26; reference numeral 28 denotes a slide assembly for adjusting the wrap-angle between said rod 21 and tape 22; reference numeral 29 denotes cartridge heater; and reference numeral 30 denotes a dead weight attached to one end of said tape 22. Bhushan's testing method is as follows. Bhushan first wrapped magnetic recording tape 22 which has dead weight 30 attached to one end, around said rod 21 made of the head material. The other end of tape 22 was then mounted on tension meter 24 which is moved by motor 26. When tension meter 24 is stationary, the tension applied by dead weight 30 would be indicated by tension meter 24. However, when tension meter 24 is moved upwardly, the friction between tape 22 and rod 21 made of head material results in a higher tension reading value. At this point, the following formula for the friction coefficient between tape 22 and rod 21 may be derived. [B. Bhushan, Wear, 93 (1984)81]

$$\mu = \frac{1}{\theta} \ln \frac{T_1}{T_0} \quad (1)$$

In said equation 1, $\theta$ is the wrap-angle, $T_0$ is the tension applied by dead weight 30, and $T_1$ is the tension value measured when tension meter 24 is moving upward.

On the other hand, where tension meter 24 is moved downward, a lower tension reading results. The relationship between the difference in tension reading values obtained from the above two conditions and the friction coefficient is indicated as follows.

$$\mu = \frac{1}{\theta} \ln \left[ \frac{F_2 - F_1}{2T} + \left\{ 1 + \frac{(F_2 - F_1)^2}{(2T)^2} \right\}^{1/2} \right] \quad (2)$$

Here, $F_2$ and $F_1$ are the tension readings when tension meter 24 is moved upwardly and downwardly, respectively; and T is the applied tension.

The conditions for friction coefficient measuring used in the apparatus according to the present invention differs from the apparatus by Bhushan in that the tape is fixed and that the cylindrical specimen is rotating. However, since the mechanics are the same, equation (2) may be also used to calculate the friction coefficient in the apparatus of the present invention. Applying equation (2) to the present invention, $F_2$ is the tension in the opposite direction of the specimen's rotation and $F_1$ is the tension in the specimen's rotation direction. The technical features and effects of the method and apparatus of the present invention may be better understood through the following examples.

EXAMPLE 1

Figure 4:
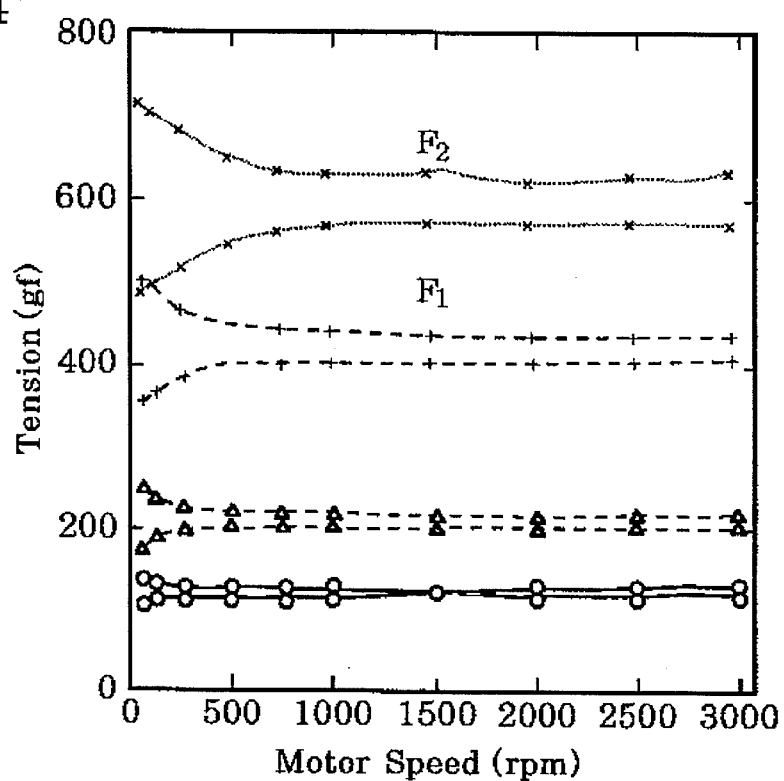
FIG. 4 is a graph showing the results of the tension measurement observed between a VTR head drum and VTR tape using another embodiment of the present invention. This graph shows changes in measured tension according to variations in drum rotation speed at various applied tensions.
Figure 5:
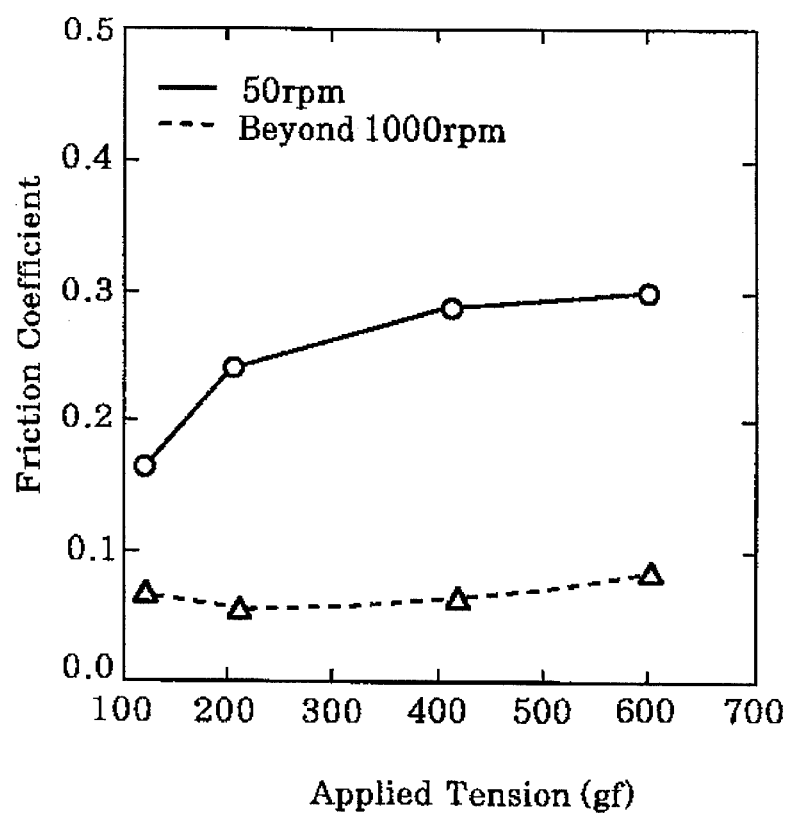
FIG. 5 is a graph of friction coefficients calculated by using the measurement results of FIG. 4.

A VTR head drum with a diameter of 60 mm was mounted. The VTR tape was wrapped, and upon applying tensions of 100 gf, 200 gf, 400 gf, and 600 gf, the resulting tension was measured at various rotation speeds. FIG. 4 shows the change in measured tension values corresponding to the change in rotation speed. At low rotation speeds, the difference in tension readings is great. However, as the rotation speed increases, the difference in tension readings decreases. When the rotation speed is above approximately 1000 rpm, the difference in tension readings is constant, unaffected by changes in the rotation speed. This indicates that as the rotation speed increases, an air gap is formed between the tape and the head drum surface, decreasing the friction between tape and head drum. Also, it indicates that after the air gap is formed, the friction property is constant, regardless of the rotation speed. Thus, this apparatus may be used for both evaluating contact friction coefficients and for testing the conditions for the formation of air gaps. As shown in FIG. 4, the difference of the tension reading at low rotation speeds increases as the applied tension is increased. At the same time, it can also be seen that the critical rotation speed, at which the air gap is completely formed, also increases. FIG. 5 shows the dependency of the friction coefficient, calculated using equation (2) and the tension readings, on the applied tension. The calculated figure at 50 rpm is a contact friction coefficient estimated at conditions where the air gap has not been formed. The calculated figure at 1,000 rpm is the friction coefficient observed after the air gap has been completely formed. At air gap formation, the friction coefficient is approximately 0.06 and does not depend on the applied tension. On the other hand, the contact friction coefficient ranges between 0.25 and 0.3 where the applied tension is more than 200 gf and it can also be observed that it does not depend greatly on the applied tension.

EXAMPLE 2

Figure 6A:
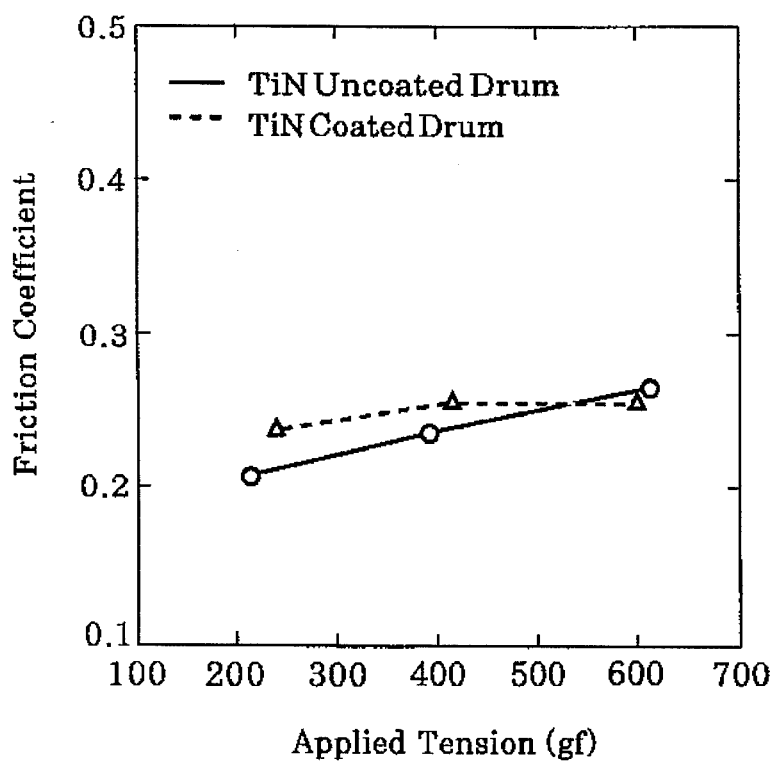
FIG. 6 is a graph showing the relationship between the applied tension and the friction coefficients of a head drum coated with TiN and a non-coated head drum before and after the testing.
Figure 6B:
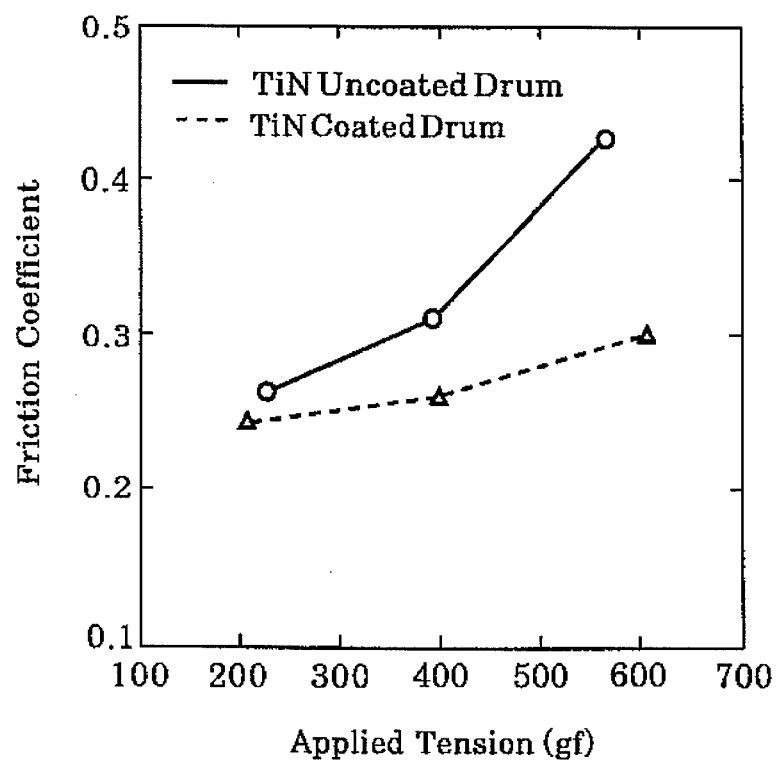

To evaluate the abrasion properties of TiN-coated VTR head drums and non-TiN-coated VTR head drums, after each of the drums were installed, the applied tension and the rotation speed were varied to estimate the friction coefficient. Further, 400 gf of tension was applied to conduct abrasion testing. Afterwards, the applied tension and rotation speed were again varied to estimate the friction coefficient. The friction coefficients before and after the abrasion testing were then relative. For the abrasion testing conditions, at a rotation speed of 3000 rpm, stationary and rotation periods of 10 seconds were repeated over 4 hours, to achieve contact between the tape and the head drum surface. FIG. 6 shows the change in the contact friction coefficient at 50 rpm before and after the abrasion testing. Before the abrasion testing, the contact friction coefficients for both the coated and uncoated drums were approximately 0.2 and there was almost no dependency on the applied tension. However, the estimated friction coefficient shows a significant difference after abrasion testing. For the uncoated drum, the friction coefficient has very high values, between 0.25 and 0.4, and has a great dependency on the applied tension. Thus, it can be seen that for uncoated drums, a significant amount of surface damage results from the present abrasion testing. This was also verified after the testing by microscopic observation of the surface. For TiN-coated drums, almost no surface damages resulted from the abrasion testing. However, for uncoated drums, it was observed that magnetic particles from the magnetic tape were imbedded in the drum surface.

What is claimed is:

1. A method for testing an abrasion property and evaluating friction coefficient for a cylindrical specimen around of which circumferential surface a relative specimen of flexible material is wrapped, comprising the following steps of:
    (a) wrapping the relative specimen of the flexible material around the circumferential surface of the cylindrical specimen so that at least some portion of the flexible material is in contact with the circumferential surface of the cylindrical specimen;
    (b) applying a predetermined tension to the relative specimen;
    (c) rotating the cylindrical specimen while the relative specimen remains stationary;
    (d) measuring tensions at both ends of the relative specimen;
    (e) evaluating the difference between the tension values at both ends of the relative specimen; and
    (f) evaluating the friction coefficient between the circumferential surface of the cylindrical specimen and the relative specimen using the difference of the tension values.

2. The method according to claim 1, wherein in the step (a) of wrapping the relative specimen around the cylindrical specimen, the contacting area between the cylindrical specimen and the relative specimen is adjustable.

3. The method according to claim 1, wherein in the step (c) of rotating the cylindrical specimen, said cylindrical specimen is rotated so that it alternates between a stationary condition and a rapidly rotating condition to achieve a physically complete contact between the cylindrical specimen and the relative specimen even when the rotation speed of said specimen is high.

4. The method according to claims 1, 2 or 3, wherein the method repeats said steps (a) to (f) while varying the rotation speed of the cylindrical specimen.

5. An apparatus for testing an abrasion property and evaluating friction coefficient for a cylindrical specimen around of which circumferential surface a relative specimen of flexible material is wrapped, comprising a mounting section, for mounting cylindrical specimen and relative specimen, said mounting section including a means for rotating the cylindrical specimen, a first and a second tension meter for measuring tensions of both ends of the relative specimen, and a tension meter support for support the first and the second tension meter, whereby the friction coefficient between the circumferential surface of cylindrical specimen and the relative specimen is evaluated by using the differences in tension values of the first and the second tension meters of the mounting section when the cylindrical specimen is rotated.

6. The apparatus according to claim 5, further comprising tie bars which are installed spaced in parallel at a fixed distances from the circumferential surface of the cylindrical specimen with the cylindrical specimen being positioned therebetween and of which position can be adjustable, the relative specimen being passed through said tie bar and being wrapped around the specimen, the contact area between cylindrical specimen and the relative specimen being adjusted by adjusting the position of the tie bar.

7. The apparatus according to claims 5 or 6, wherein the tension meter support on which tension meters are mounted is movable forward or backward with respect to the relative specimen to adjust the tension to be applied to the relative specimen.

8. The apparatus according to claim 5, wherein the means for rotating the cylindrical specimen comprises a control means for controlling rotating speed such that the cylindrical specimen alternates between a stationary condition and a rapidly rotating condition to achieve a substantial contact between the cylindrical specimen and the relative specimen even when the rotation speed of the cylindrical specimen is high.

* * * * *